United States Patent
Denk et al.

(10) Patent No.: US 9,550,059 B2
(45) Date of Patent: Jan. 24, 2017

(54) RESPIRATION SENSORS FOR RECORDING OF TRIGGERED RESPIRATORY SIGNALS IN NEUROSTIMULATORS

(71) Applicant: MED-EL Elektromedizinische Geraete GmbH, Innsbruck (AT)

(72) Inventors: Christian Denk, Innsbruck (AT); Birthe Rubehn, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/677,121

(22) Filed: Apr. 2, 2015

(65) Prior Publication Data

US 2015/0306384 A1   Oct. 29, 2015

Related U.S. Application Data

(60) Provisional application No. 61/984,914, filed on Apr. 28, 2014.

(51) Int. Cl.
*A61N 1/36* (2006.01)
*A61N 1/05* (2006.01)

(52) U.S. Cl.
CPC ......... *A61N 1/3601* (2013.01); *A61N 1/36139* (2013.01); *A61N 1/0517* (2013.01); *A61N 1/0519* (2013.01); *A61N 1/3611* (2013.01)

(58) Field of Classification Search
CPC   A61N 1/3601; A61N 1/3611; A61N 1/36135; A61N 1/36078
USPC .......................................................... 607/42
See application file for complete search history.

(56) References Cited

U.S. PATENT DOCUMENTS

| | | | |
|---|---|---|---|
| 5,056,519 A | 10/1991 | Vince | |
| 6,251,126 B1 | 6/2001 | Ottenhoff et al. | |
| 7,734,351 B2 * | 6/2010 | Testerman | A61N 1/36007 607/48 |
| 8,136,532 B2 | 3/2012 | Lindenthaler et al. | |
| 2006/0282127 A1 * | 12/2006 | Zealear | A61B 5/087 607/42 |

(Continued)

OTHER PUBLICATIONS

Thermal conduction of titanium implants under CO2 laser irradiation in vitro; Linder et al; Ann Maxillofac Surg. Jan.-Jun. 2012; 2(1): 12-16.*

(Continued)

*Primary Examiner* — Paula J Stice
(74) *Attorney, Agent, or Firm* — Sunstein Kann Murphy & Timbers LLP

(57) ABSTRACT

A respiration implant system for a patient with impaired breathing includes one or more temperature sensors configured for placement into an inner wall tissue along an airway passage of the patient and configured to measure temperature in the inner wall tissue in order to produce a temperature signal based on the measured temperature. The system further includes a pacing processor configured to receive the temperature signal from the temperature sensor and to generate a respiration pacing signal based on the temperature signal that is synchronized with a breathing cycle of the patient and a stimulating electrode configured to deliver the respiration pacing signal from the pacing processor to respiration neural tissue of the patient to facilitate breathing in the patient. The respiration implant system may be used as a laryngeal pacemaker system.

18 Claims, 5 Drawing Sheets

(56) References Cited

U.S. PATENT DOCUMENTS

| | | | |
|---|---|---|---|
| 2008/0103545 A1* | 5/2008 | Bolea | A61N 1/0556 607/42 |
| 2008/0208280 A1 | 8/2008 | Lindenthaler et al. | |
| 2010/0076518 A1* | 3/2010 | Hlavka | A61N 1/3601 607/42 |
| 2011/0264164 A1 | 10/2011 | Christopherson et al. | |
| 2012/0150255 A1 | 6/2012 | Lindenthaler et al. | |

OTHER PUBLICATIONS

International Searching Authority—International Search Report—International Application No. PCT/US15/24018, dated Jul. 2, 2015, together with the Written Opinion of the International Searching Authority, 14 pages.

* cited by examiner

RESPIRATION SENSORS FOR RECORDING OF TRIGGERED RESPIRATORY SIGNALS IN NEUROSTIMULATORS

CROSS REFERENCE TO RELATED APPLICATIONS

The present application claims priority to U.S. Provisional Patent Application No. 61/984,914 filed Apr. 28, 2014, the disclosure of which is incorporated by reference herein in its entirety.

TECHNICAL FIELD

The present invention relates to respiration implant systems such as implantable respiration pacing systems and sleep apnea treatment systems.

BACKGROUND ART

The larynx is located in the neck and is involved in breathing, producing sound (speech), and protecting the trachea from aspiration of food and water. FIG. 1A shows a posterior view of the anatomy of a human larynx 100 and FIG. 1B shows the larynx as viewed from above, including the epiglottis 101, thyroid cartilage 102, vocal folds/ligaments 103, cricothyroid muscle 104, arytenoid cartilage 105, posterior cricoarytenoid (PCA) muscle 106, vocalis muscle 107, cricoid cartilage 108, recurrent laryngeal nerve (RLN) 109, transverse arytenoid muscle 110, oblique arytenoid muscle 111, superior laryngeal nerve 112, hyoid bone 113 (note: the hyoid bone is not usually considered part of the larynx and is included in FIGS. 1A and 1B strictly as an aid to orientation), thyrohyoid membrane 117, and thicker lower portion of elastic membrane or conus elasticus 118. FIG. 1C shows a lateral view and FIG. 1D shows a sagittal sectional view of head and neck regions showing the larynx 100 and its structures, trachea 114, esophagus 115 and pharynx 116, including cricoarytenoid joint 119, cricothyroid joint 120, and tongue 121.

The nerves and muscles of the larynx 100 abduct (open) the vocal folds 103 during the inspiration phase of breathing to allow air to enter the lungs. And the nerves and muscles of the larynx 100 adduct (close) the vocal folds 103 during the expiration phase of breathing to produce voiced sound. At rest, respiration frequency typically varies from 12 to 25 breaths per minute. So, for example, 20 breaths per minute result in a 3 second breath duration, with 1.5 sec inspiration, and 1.5 sec exhalation phase (assuming a 50/50 ratio). The breathing frequency changes depending on the physical activity.

Unilateral and bilateral injuries or ruptures of the recurrent laryngeal nerve (RLN) 109 initially result in a temporal partial paralysis of the supported muscles in the larynx (and the hypolarynx). A bilateral disruption of the RLN 109 causes a loss of the abductor function of the posterior cricoarytenoid (PCA) muscle 106 with acute asphyxia and life-threatening conditions. This serious situation usually requires surgical treatment of the bilateral vocal cord paralysis such as cordotomy or arytenoidectomy, which subsequently restrict the voice and put at risk the physiologic airway protection.

Another more recent treatment approach to RLN injuries uses a respiration implant that electrically stimulates (paces) the PCA muscle 106 during inspiration to abduct (open) the vocal folds 103. During expiration, the vocal folds 103 relax (close) to facilitate voicing. In these respiration implant systems, the patient can adjust (vary) the pacing/respiration frequency (breaths per minute) according to his or her physical state (e.g., at rest, normal walking, stairs, etc.) by manually switching the stimulation frequency of the pacer device, the assumption being that the human body may adapt to the artificial externally applied respiration frequency—within some locking-range. Thus, the patient and the respiration pacemaker can be described as free running oscillators at almost the same frequency but without phase-matching (no phase-locking). At some time, both systems will be in phase, but at other times the systems will be out of phase and thus benefit for the patient will be reduced.

Besides laryngeal pacemakers for RLN injuries, there also are respiration implant neurostimulators that electrically stimulate the hypoglossal nerve that innervates the root of the tongue for treatment of sleep apnea. These sleep apnea treatment systems use a respiration sensor that is implemented to trigger on the inhaling phase of breathing, for example, using a bioimpedance measurement or a pressure sensor in the pleural gap.

SUMMARY

Embodiments of the present invention are directed to a respiration implant system (e.g., laryngeal pacemaker systems) for a patient with impaired breathing. The system includes one or more temperature sensors configured for placement into an inner wall tissue along an airway passage of the patient, e.g., inside the mucosa along the laryngeal walls, and configured to measure temperature in the inner wall tissue in order to produce a temperature signal based on the measured temperature. The system further includes a pacing processor configured to receive the temperature signal from the temperature sensor and to generate a respiration pacing signal based on the temperature signal that is synchronized with a breathing cycle of the patient, and a stimulating electrode configured to deliver the respiration pacing signal from the pacing processor to respiration neural tissue of the patient to facilitate breathing in the patient.

Embodiments of the present invention are also directed to methods of using a respiration implant system in order to develop a respiration pacing signal in a patient with impaired breathing to promote breathing in the patient. The method includes using one or more temperature sensors implanted into an inner wall tissue along an airway passage of the patient to measure temperature in the inner wall tissue along the airway passage and developing a temperature signal based on the measured temperature and a breathing cycle of the patient. The method further includes generating a respiration pacing signal based on the temperature signal that is synchronized with the breathing cycle of the patient and delivering the respiration pacing signal to respiration neural tissue of the patient to facilitate breathing in the patient.

In related embodiments, the temperature sensors may be placed subglottically inside the inner wall tissue along the airway passage. For example, the temperature sensors may be placed into the thyrohyoid membrane between the cricoid cartilage and the thyroid cartilage of the patient. Preferably, the temperature sensors have a reaction time of about 1° C. change per 5 ms or faster and have a temperature resolution of about 0.05° C. or smaller. The temperature sensors may be coupled to the stimulating electrode. The measured temperature may be based on inspired air in the airway passage and/or expired air in the airway passage. The stimulating electrode may be configured to deliver the respiration pacing signal to posterior cricoarytenoid muscle in the larynx.

The respiration implant system may be used as a laryngeal implant system and the stimulating electrode may deliver the respiration pacing signal to posterior cricoarytenoid muscle in the larynx, the hypoglossal nerve, and/or the internal superior laryngeal nerve (iSLN).

DETAILED DESCRIPTION

Various embodiments of the present invention are directed to improved respiration implants that use one or more temperature sensors implanted into an inner wall tissue along an airway passage (e.g., along the pharynx, the larynx and/or the trachea) of the patient and configured to measure temperature in the inner wall tissue along the airway passage. For example, the inner wall tissue may change temperature based on the temperature of the inspired and/or expired air within the airway passage. Based on this measured temperature, a temperature signal is produced and used to generate a respiration pacing signal that is synchronized with a breathing cycle of the patient. A stimulating electrode then delivers the respiration pacing signal to respiration neural tissue, e.g., posterior cricoarytenoid muscle in the larynx of the patient, the hypoglossal nerve and/or internal superior laryngeal nerve, to facilitate breathing in the patient. Such respiration implant systems include, for example, laryngeal pacemaker systems.

Embodiments of the present invention utilize the underlying effect that the air in the airway passage varies in temperature depending on the phase of the breathing cycle. For example, in general, inspired air is colder than the airway passage and is thus heated up in the airway passage during the inhalation phase of breathing. Therefore, under most circumstances, there is a temperature difference between inhaled and exhaled air so that colder air is inhaled than exhaled. These temperature differences can be easily measured inside the inner wall tissue of the airway passage from the nose/mouth until the lungs e.g., along the tracheobronchial tree. This necessary heat exchange during inspiration comes from the mucosa, or inner wall tissue that covers the muscles of the larynx, along the surface of the airway passage that heats up the colder air. Heat moves from the mucosa to the incoming air as a direct function of the temperature difference that exists between the airstream and the mucosa throughout the airway passage. During expiration, the process reverses. The air exiting the alveoli is now warmer than the mucosa and during its passage to the mouth, heat from the air is continuously given back to the airway passage surface. Thus, the inner wall tissue changes temperature based on the temperature of the inspired and/or expired air within the airway passage.

Figure 1A:
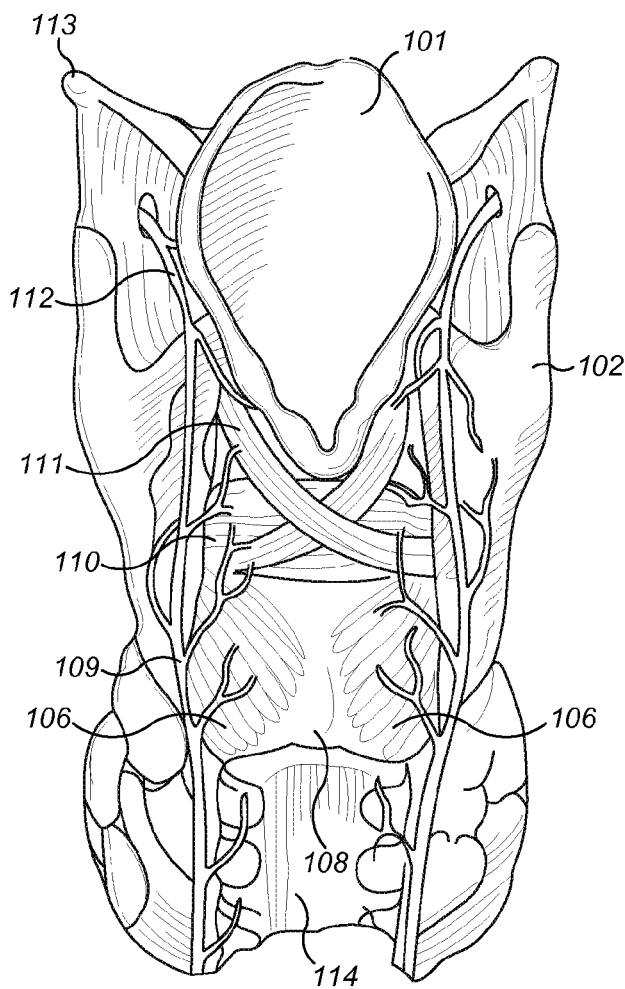
FIG. 1A shows a posterior view and FIG. 1B shows a superior view of the anatomy of a human larynx.
Figure 1B:
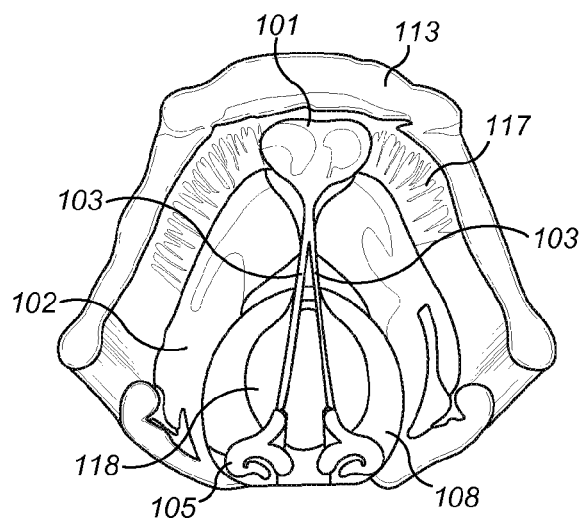
Figure 1C:
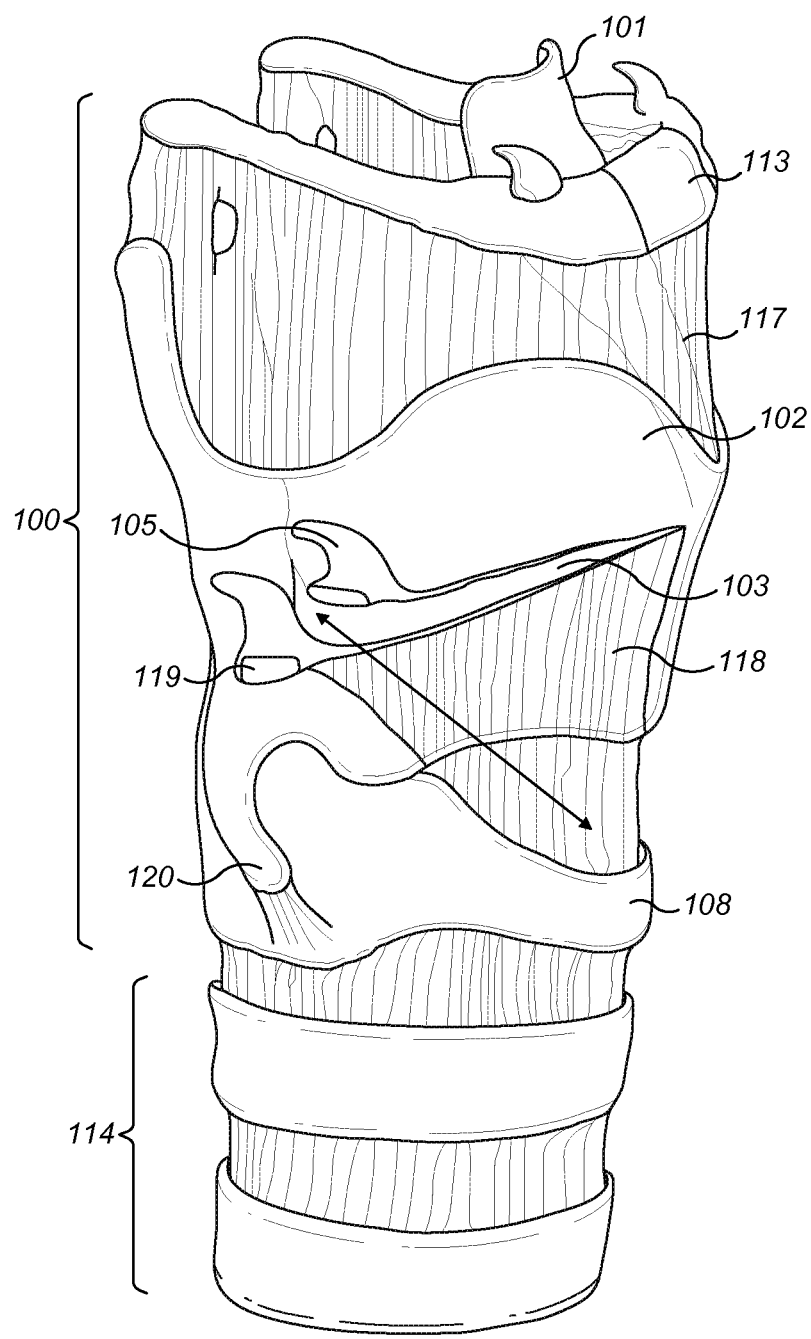
FIG. 1C shows a lateral view and FIG. 1D shows a sagittal sectional view of head and neck regions showing the larynx, trachea, and esophagus.
Figure 1D:
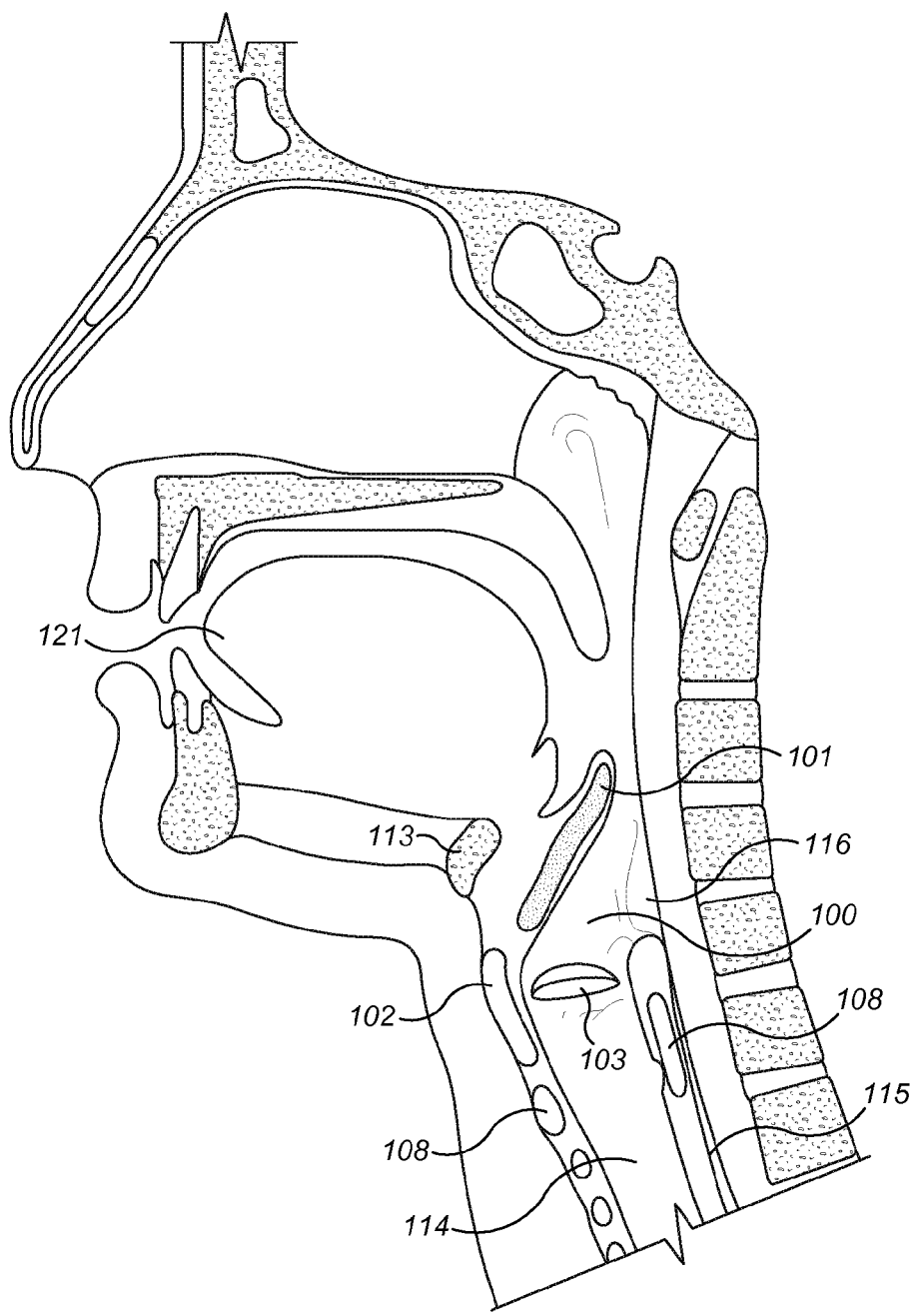
Figure 2:
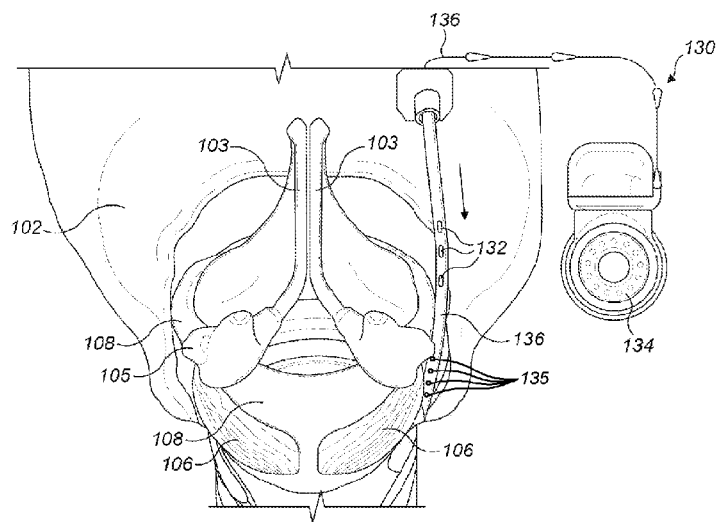
FIG. 2 shows a respiration implant system with a stimulating electrode placed into posterior cricoarytenoid (PCA) muscle according to embodiments of the present invention.

FIG. 2 shows one embodiment of a respiration implant system 130 having one or more temperature sensors 132 implanted along an airway passage of the patient. The temperature sensor(s) 132 are configured to measure the temperature in the inner wall tissue along the airway passage (i.e., along the pharynx, the larynx and/or the trachea) in order to produce a temperature signal based on the measured temperature. Preferably, the temperature sensor(s) have a fast reaction time (e.g., 1° C. change per 5 ms or faster) which is very short compared to the inhalation and exhalation periods and good temperature resolution (e.g., 0.05° C. or smaller) so that the drop in temperature is detected by the temperature sensor(s) 132 at the onset of the inhalation phase, and similarly the rise in temperature is detected by the temperature sensor(s) 132 at the onset of the expiration phase. Preferably, the temperature sensor(s) 132 are placed into the thyrohyoid membrane (mucosa) 117 subglottically between the cricoid cartilage 108 and the thyroid cartilage 102, e.g., along the black arrow as shown in FIG. 1C. Placing the temperature sensor(s) 132 subglottically (below the separation between trachea 114 and oesophagus 115) provides the benefit of minimizing the effects produced when drinking hot beverages and should reduce any artefacts when sensing respiration.

Figure 3:
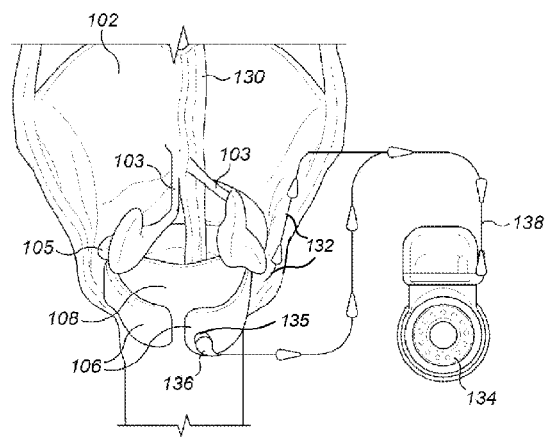
FIG. 3 shows one vocal fold opening during stimulation with a respiration implant system according to embodiments of the present invention.

The respiration implant system 130 further includes a pacing processor 134 configured to receive the temperature signal from the temperature sensor(s) 132 and configured to generate a respiration pacing signal based on the temperature signal that is synchronized with a breathing cycle of the patient. The pacing processor 134 delivers the respiration pacing signal via a processor lead 138 to a stimulating electrode 136 implanted in a target respiration neural tissue to facilitate breathing in the patient. For example, FIG. 3 shows vocal fold opening during the inhalation phase when stimulating the PCA muscle by the stimulating electrode 136. The stimulating electrode 136 may be implanted in the respiration neural tissue using a variety of insertion techniques. For example, U.S. Pat. No. 8,136,532 to Lindenthaler et al., incorporated by reference herein in its entirety, discloses various methods of introducing a stimulating electrode to interface with laryngeal structures, such as the PCA muscle. The placement of the temperature sensor(s) 132 inside the mucosa may be along the same insertion path as the stimulating electrode 136. Therefore, the temperature sensor(s) 132 may be placed on the outer surface of the stimulating electrode 136, so that no additional temperature sensor electrode is necessary, and no additional branch off of the stimulating electrode 136 with the temperature sensor(s) is necessary either. In this case, the stimulating electrode contact(s) 135 and temperature sensor(s) 132 are located on one stimulating electrode 136, with no separation of functionality on another branch of the electrode, which permits the placement of the stimulating electrode 136 without the problems of sensing and stimulating the same physical position. In other embodiments, the temperature sensor(s) 132 and the stimulating electrode contact(s) 135 may be on separate electrode branches.

Figure 4:
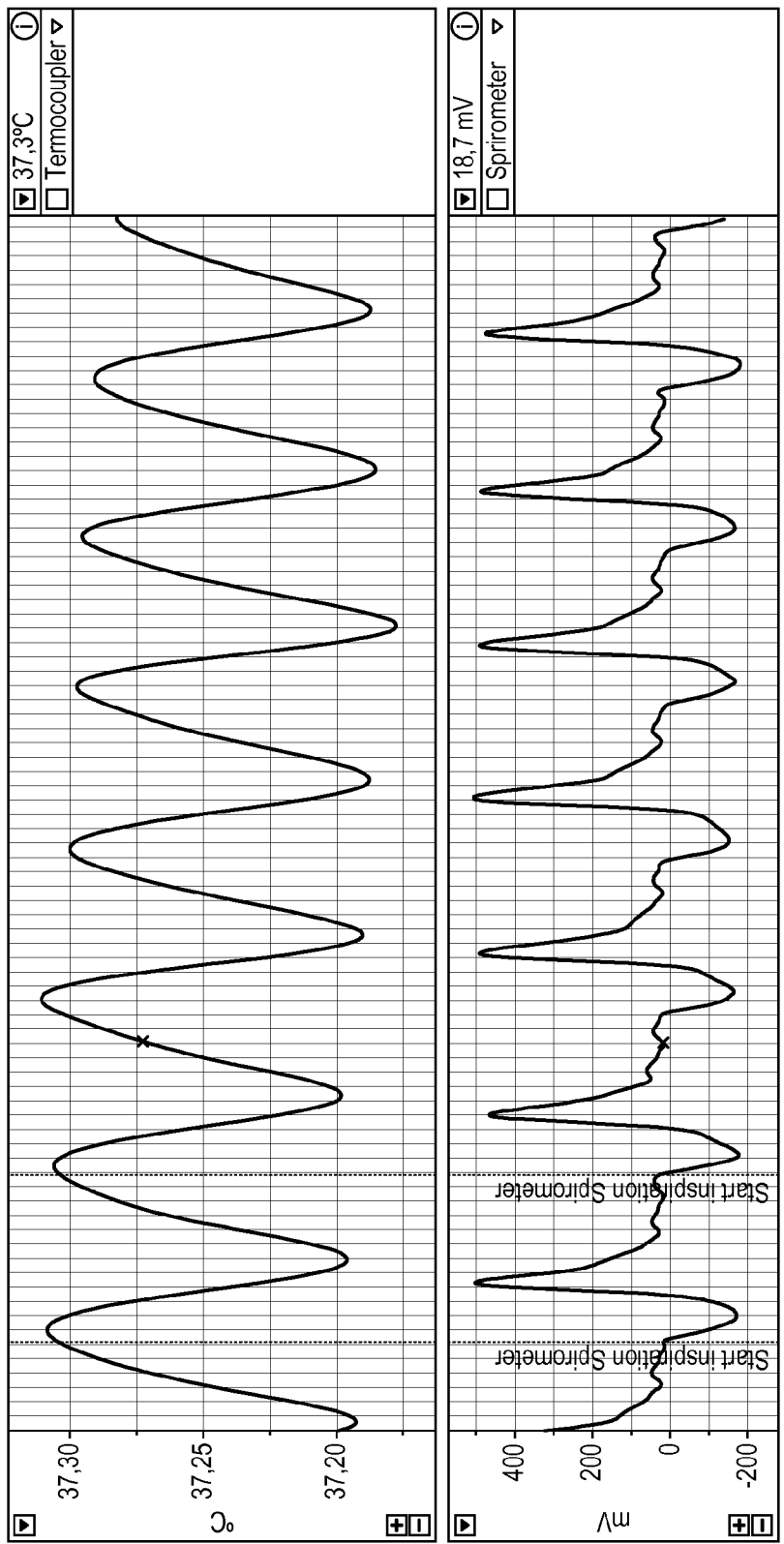
FIG. 4 shows waveforms for the temperature change and breathing cycle for a temperature sensor compared to reference signal waveforms.

FIG. 4 shows waveforms for the temperature change and breathing cycle for a temperature sensor placed intramucosally or within the inner wall tissue along the airway passage compared to a reference signal waveform. The first (top) waveform was formed with a temperature signal from a temperature sensor placed subglottically inside the mucosal wall. The second (bottom) waveform was formed with a Spirometer reference signal to define inspiration and expiratory cycles. The two vertical dashed lines near the beginning of the waveforms show the start of each inspiration cycle. The temperature signal shows a high correlation in temperature decrease during inspiration and temperature increase during expiration. The measured delay between temperature sensors placed intratracheal and intramucosal was around 100-300 ms depending on the respiratory pattern. This delay may be due to the fact that tissues need more time to be cooled down by the airstream than the airstream itself. The amplitude of temperature difference measured was around 0.2-0.4° C. between inspiration and expiration. This demonstrates that a temperature sensor with high sensitivity (e.g., resolution of about 0.05° C. or smaller) placed within the mucosal wall can detect the breathing cycle and can be used as a trigger for any respiratory neurostimulator.

The pacing processor 134 can use signal processing of the temperature signal from the temperature sensor 132 to detect the onset of inspiration. For example, the peak or change point of the temperature signal can be used as a stimulation trigger for a stimulation pulse for patients with unilateral or bilateral vocal fold paralysis. The stimulation trigger signal defines a specific time point during the respiration cycle to initiate stimulation of the target neural tissue. The time point may specifically be the start or end of the inspiratory or expiratory phase of breathing, or any other defined time point. The respiration pacing signal is then generated to synchronize the respiration implant system 130 to the breathing cycle of the patient.

In addition to the temperature sensor(s) 132, the respiration implant system 130 may also include other sensors that may be used to detect the breathing cycle and the onset of inspiration in order to synchronize the timing of the respiration implant system 130 to the breathing cycle of the patient. These sensors may include, for example, various microphones, accelerometer sensors, and pressure sensors (positioned in the pleura gap). For example, a three-axis acceleration movement sensor (not shown) may be located within the housing of the pacing processor 134 and may be used to generate a movement signal. Electromyogram (EMG) measurements may also be used to detect the onset of inspiration. These respiration sensors may be used to generate a respiration signal and/or movement signal that is used in conjunction with, or instead of, the temperature signal in order to detect the breathing cycle and the onset of inspiration. For example, in an environment where the surrounding air has about the same temperature as the body itself, the temperature sensor(s) 132 may not provide reliable sensor signals if there is no temperature difference to detect. In this case, one or more additional respiration sensors may provide the respiration implant system 130 with alternative sensor(s) to detect the breathing cycle, and the pacing processor 134 may generate the respiration pacing signal based on the temperature signal, the respiration signal and/or the movement signal in order to synchronized the respiration implant system 130 with the detected breathing cycle of the patient. Alternatively, or in addition, the respiration implant system 130 may be configured to switch to a sensorless operation mode in which the stimulation rate for opening the vocal folds is predetermined or is derived from previous sensing cycle(s).

Embodiments of the invention may be implemented in part in any conventional computer programming language such as VHDL, SystemC, Verilog, ASM, etc. Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of software (e.g., a computer program product), hardware, and/or firmware. Still other embodiments of the invention may be implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A respiration implant system for a patient with impaired breathing, the system comprising:
   one or more temperature sensors configured for placement subglottically inside an inner wall tissue along an airway passage of the patient and configured to measure temperature in the inner wall tissue in order to produce a temperature signal based on the measured temperature;
   a pacing processor configured to receive the temperature signal from the temperature sensor and to generate a respiration pacing signal based on the temperature signal that is synchronized with an onset of (1) an inhalation phase, (2) an exhalation phase, or (3) the inhalation phase and the exhalation phase of a breathing cycle of the patient; and
   a stimulating electrode having one or more contacts configured to deliver the respiration pacing signal from the pacing processor to respiration neural tissue of the patient to facilitate breathing in the patient, wherein the one or more temperature sensors and the one or more contacts are located on the stimulating electrode.

2. The system according to claim 1, wherein the one or more temperature sensors are configured for placement into thyrohyoid membrane of the patient.

3. The system according to claim 1, wherein the one or more temperature sensors have a reaction time of 1° C. change per 5 ms or faster.

4. The system according to claim 1, wherein the one or more temperature sensors have a temperature resolution of 0.05° C. or smaller.

5. The system according to claim 1, wherein the one or more temperature sensors are located on one branch of the stimulating electrode and the one or more contacts are located on another branch of the stimulating electrode.

6. The system according to claim 1, wherein the measured temperature is based on inspired air in the airway passage, expired air in the airway passage, or a combination thereof.

7. The system according to claim 1, wherein the stimulating electrode is configured to deliver the respiration pacing signal to posterior cricoarytenoid muscle in the larynx.

8. The system according to claim 1, wherein the stimulating electrode is configured to deliver the respiration pacing signal to hypoglossal nerve and/or internal superior laryngeal nerve.

9. A method of developing a respiration pacing signal in a patient with impaired breathing to promote breathing in the patient, the method comprising:
    using one or more temperature sensors implanted subglottically inside an inner wall tissue along an airway passage of the patient to measure temperature in the inner wall tissue along the airway passage;
    developing a temperature signal based on the measured temperature;
    generating a respiration pacing signal based on the temperature signal that is synchronized with an onset of (1) an inhalation phase, (2) an exhalation phase, or (3) the inhalation phase and the exhalation phase of a breathing cycle of the patient; and
    delivering the respiration pacing signal, using one or more contacts on a stimulating electrode, to respiration neural tissue of the patient to facilitate breathing in the patient, wherein the one or more temperature sensors and the one or more contacts are located on the stimulating electrode.

10. The method according to claim 9, wherein the one or more temperature sensors are implanted into thyrohyoid membrane of the patient.

11. The method according to claim 9, wherein the one or more temperature sensors have a reaction time of 1° C. change per 5 ms or faster.

12. The method according to claim 9, wherein the one or more temperature sensors have a temperature resolution of 0.05° C. or smaller.

13. The method according to claim 9, wherein the one or more temperature sensors are located on one branch of the stimulating electrode and the one or more contacts are located on another branch of the stimulating electrode.

14. The method according to claim 9, wherein the measured temperature is based on inspired air in the airway passage, expired air in the airway passage, or a combination thereof.

15. The method according to claim 9, wherein the respiration neural tissue of the patient includes posterior cricoarytenoid muscle in the larynx.

16. The method according to claim 9, wherein the respiration neural tissue of the patient includes hypoglossal nerve and/or internal superior laryngeal nerve.

17. The system according to claim 1, wherein the one or more temperature sensors are located on an outer surface of the stimulating electrode.

18. The method according to claim 9, wherein the one or more temperature sensors are located on an outer surface of the stimulating electrode.

* * * * *